United States Patent [19]

Jordan et al.

[11] Patent Number: 5,214,173

[45] Date of Patent: May 25, 1993

[54] CYCLOPENTADIENYL DICARBOLLIDE COMPLEXES OF TITANIUM, ZIRCONIUM AND HAFNIUM

[75] Inventors: Richard F. Jordan, Iowa City, Iowa; Donna J. Crowther, Baytown, Tex.

[73] Assignee: The University of Iowa Research Foundation, Iowa City, Iowa

[21] Appl. No.: 814,809

[22] Filed: Dec. 31, 1991

[51] Int. Cl.$^5$ ................................................ C07F 1/08
[52] U.S. Cl. .......................................... 556/8; 556/53; 526/134; 526/170; 502/202
[58] Field of Search .................... 526/134, 170; 556/7, 556/8, 51, 53

[56] References Cited

PUBLICATIONS

J. Am. Chem. Soc., 1989, 111, 2728–2729.
J. C. S. Chem. Commun., 1975 (20), 848–849.
Inorg. Chem., 1976, 15(11), 2872–2882.
Cationic Cp$_2$Zr(R)(L)$^+$ Complexes as Models for Metallocene-Based Ziegler–Natta Catalysts. Paper presented by Richard F. Jordan at the Apr. 26, 1990 meeting of the American Chemical Society in Boston, Mass.
J. Am. Chem. Soc., 1991, 113, 1455–1457, published Feb. 13, 1991.

Primary Examiner—Joseph L. Schofer
Assistant Examiner—David Wu
Attorney, Agent, or Firm—J. S. Piscitello

[57] ABSTRACT

Novel cyclopentadienyl dicarbollide complexes of titanium, zirconium and hafnium constitute a new class of neutral, 14-electron, d$^0$, mixed-ring, bent-metallocene alkyl complexes which are useful as polymerization catalysts.

12 Claims, No Drawings

CYCLOPENTADIENYL DICARBOLLIDE COMPLEXES OF TITANIUM, ZIRCONIUM AND HAFNIUM

FIELD OF THE INVENTION

This invention relates to novel cyclopentadienyl dicarbollide complexes of titanium, zirconium and hafnium.

BACKGROUND OF THE INVENTION

Bis(cyclopentadienyl) complexes of the general formula $Cp'_2MR_2$ wherein $Cp'$ is a substituted or unsubstituted cyclopentadienyl radical, M is Ti, Zr or Hf, and R is alkyl, are well known in the art. These complexes can be employed together with alkyl aluminum and alumoxane cocatalysts to produce active olefin polymerization catalysts. Particularly active catalysts are produced when these complexes are employed together with alumoxane cocatalysts. W. Kaminsky et al., "Polymerization Of Olefins With A Homogeneous Zirconium/Alumoxane Catalyst", *Adv. Polyolefins* [Proc. ACS Int. Symp.], Meeting Date 1985, 361-371. Edited by: Seymour, Raymond B.; Cheng, Tai. Plenum: New York, N.Y., published 1987.

It is postulated that the mechanism by which these catalyst systems polymerize olefins involves the formation of cationic d° metallocene alkyl complexes of the formula $(Cp'_2MR)^+$ which are ion paired with a negatively charged aluminumate counterion to form an active ionic catalyst system.

Bis(cyclopentadienyl) complexes having the formula $Cp'_2MX_2$ wherein $Cp'$ is as above defined and X is halogen are also well known in the art. These complexes can also be employed with alryl aluminum and alumoxane cocatalysts to produce active olefin polymerization catalysts. The activity of these catalysts is likewise attributed to formation of cationic d° metallocene alkyl complexes of the formula $(Cp'_2MR)^+$ as intermediates which then coordinate with a negatively charged counterion. In this instance the intermediate product is produced by alkylation with the aluminum cocatalyst. This catalyst system is also ionic in nature.

In both instances, the polymerization activity of the catalyst system is attributed to formation of the highly coordinatively and electronically unsaturated 14-electron $(Cp'_2MR)^+$ cation which is capable of coordinating and inserting olefins into the M-R bond. Also in both instances, a labile stabilizing anion is required to stabilize the active cation species. In addition, these systems require an undesirable excess of aluminum cocatalyst to function effectively, particularly when an alumoxane is employed as cocatalyst.

Richard F. Jordan, "Cationic Metal-Alkyl Olefin Polymerization Catalysts", *Journal of Chemical Education*, April 1988, Vol. 65, No. 4, 285-289, discloses the preparation of zirconocene complexes such as $[Cp_2Zr(CH_3)(THF)]^+[BPh_4]^-$ wherein Cp is $C_5H_5$, THF is $C_4H_8O$, and Ph is $C_6H_5$.

The discovery of these complexes made it possible to employ a metallocene complex to polymerize ethylene in the absence of an aluminum cocatalyst. However, such complexes were found to polymerize ethylene rather slowly due to the presence of THF.

Gregory G. Hlatky et al., "Ionic, Base-Free Zirconocene Catalysts for Ethylene Polymerization", *J. Am. Chem. Soc.*, 1989, 111, 2728-2729, disclose that peralkylated zirconocenes such as $Cp^*_2ZrMe_2$, wherein $Cp^*$ is $C_5Me_5$ and Me is a methyl radical, react with the diprotic carborane acid nido-$C_2B_9H_{13}$ in pentane to form ionic monomethyl complexes such as $Cp^*_2ZrMe(C_2B_9H_{12})$. The large size and chemical inertness of the high-nuclearity polyhedral carborane anion $(C_2B_9H_{12})^-$ is said to make it a compatible counterion for the cationic dicyclopentadienyl alkyl complex $(Cp^*_2ZrMe)^+$. Such complexes are also said to polymerize ethylene in the absence of an aluminum cocatalyst and to be highly active compared to the Jordan complexes.

M. Frederick Hawthorne, "The Chemistry of the Polyhedral Species Derived from Transition Metals and Carboranes", *Acc. Chem. Res.*, 1968, 1, 281 has disclosed the "sandwich" bonding of a cyclopentadienyl ion $(C_5H_5)^-$ and a (3)-1,2-dicarbollide ion $[(3)-1,2-B_9C_2H_{11}]^{2-}$ to both iron and cobalt to produce compounds of the type $[\pi-C_5H_5]Fe[\pi-(3)-1,2-B_9C_2H_{11}]$. However, these compounds have not been described as useful polymerization catalysts.

SUMMARY OF THE INVENTION

This invention relates to novel cyclopentadienyl dicarbollide complexes of the formula:

$(Cp')(C_2B_9H_{11})M(CH_3)$ wherein:

Cp' is an unsubstituted, alkyl-substituted, or fused ring cyclopentadienyl radical, and M is Ti, Zr or Hf.

While (Cp') can be a fused ring cyclopentadienyl radical, such as indenyl and fluorenyl, it is preferably an unsubstituted or alkyl-substituted cyclopentadienyl radical. Thus, (Cp') is preferably $(C_5R_5)$ wherein R is, independently, hydrogen or an alkyl radical containing from 1 to 6 carbon atoms. Most preferably, Cp' is $(C_5H_5)$ or $[C_5(CH_3)_5]$.

The (Cp') group in the above formula represents a uninegative cyclopentadienyl ligand, and the $(C_2B_9H_{11})$ group represents a dinegative dicarbollide ligand. The isomeric $(C_2B_9H_{11})^=$ ligands are commonly known by the trivial names, 1,2-dicarbollide and 1,7-dicarbollide, in accordance with the nomenclature described by M. Frederick Hawthorne et al., "$\pi$-Dicarbollyl Derivatives of the Transition Metals. Metallocene Analogs", *J. Am. Chem. Soc.*, 1968, 90, 879-896. This nomenclature is employed throughout the present specification in reference to these ligands.

DETAILED DESCRIPTION OF THE INVENTION

The novel cyclopentadienyl dicarbollide complexes of the present invention constitute a new class of neutral, 14-electron, d°, mixed-ring, bent-metallocene alkyl complexes. By substituting the isolobal, dinegative dicarbollide ligand $(C_2B_9H_{11})^=$ for the uninegative cyclopentadienyl ligand $(Cp')^-$ of the typical cationic metallocene alkyl complex, $[(Cp')_2MR]^+$, the overall charge is reduced by 1 unit and a neutral rather than a charged complex is produced, while at the same time leaving the gross structural and metal frontier orbital properties of the complex unchanged. As a consequence, the new complexes do not require a cocatalyst, such as an alkylalumoxane, to generate an active polymerization catalyst.

The novel cyclopentadienyl dicarbollide complexes of the present invention can be prepared by the reaction of the diprotic carborane acid nido-$C_2B_9H_{13}$ and a cyclopentadienyl metallocene complex of the formula $(Cp')M(CH_3)_3$, wherein $Cp'$ and M are as defined above. The $C_2B_9H_{13}$ carborane contains two acidic hydrogen ions which readily cleave the metal-carbon bonds of electrophilic metals. The reaction of $C_2B_9H_{13}$ and $(Cp')M(CH_3)_3$ can be illustrated by the following equation:

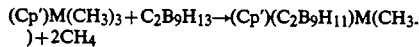

The compounds employed as starting materials in preparing the novel complexes of the present invention are known materials and can be prepared in accordance with procedures customarily employed for preparing such compounds.

When preparing the cyclopentadienyl dicarbollide complexes of the present invention, it is preferred to employ equimolar amounts of $C_2B_9H_{13}$ and $(Cp')M(CH_3)_3$. Lesser amounts of $C_2B_9H_{13}$, for example as little as 0.5 mole of $C_2B_9H_{13}$ per mole of $(Cp')M(CH_3)_3$ present, can also be employed; however, such proportions of reactants do not provide any advantage compared to the use of equimolar amounts of reactants.

Reaction between $C_2B_9H_{13}$ and $(Cp')M(CH_3)_3$ readily occurs at temperatures ranging from as low as about $-100°$ C. to as high as about $25°$ C. However, because the resulting cyclopentadienyl dicarbollide complexes undergo increasing intermolecular reaction to produce methylene-bridged derivatives as the temperature rises, as described below, it is preferred to effect reaction at temperatures below $23°$ C. Most preferably, the reactants are mixed below $0°$ C. and then warmed to $23°$ C.

Atmospheric pressure may be employed in effecting reaction between $C_2B_9H_{13}$ and $(Cp')M(CH_3)_3$, or reduced pressure may be employed if desired to assist in methane degasification. An inert atmosphere should be maintained to prevent oxidation from occurring. By an "inert atmosphere" is meant an atmosphere which is non-reactive under the conditions of the reaction.

Reaction between $C_2B_9H_{13}$ and $(Cp')M(CH_3)_3$ is effected in an inert liquid solvent. By an "inert liquid solvent" is meant a liquid solvent in which the reactants are soluble to an extent whereby they are brought into reactive contact and which itself is non-reactive under the conditions of the reaction. Suitable inert liquid solvents which can be employed for this purpose include hydrocarbons such as hexane, cyclohexane, heptane, benzene, toluene and the like. In general, an amount of solvent ranging from 1 to about 20 times, preferably from 10 to 15 times, the weight of reactants can be effectively employed. Greater amounts of solvent can also be employed; however, such amounts of solvent do not provide the advantages obtainable by operating within the range indicated.

The novel cyclopentadienyl dicarbollide complexes of the present invention undergo intermolecular reaction on standing to produce methylene-bridged derivatives having the formula:

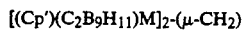

wherein M and R are as defined above.

The reaction which occurs can be illustrated by the equation:

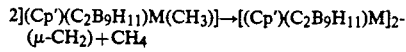

The methylene-bridged complexes produced in this manner consist of two mixed-ring bent-metallocene centers linked by the $\mu$-$CH_2$ group.

The cyclopentadienyl dicarbollide complexes of zirconium are less stable than the hafnium complexes. Thus, for example, the $[C_5(CH_3)_5][C_2B_9H_{11}]Zr(CH_3)$ complex can be quantitatively converted to the methylene-bridged derivative by thermolysis in toluene at $45°$ C. for two hours. The corresponding $[C_5(CH_3)_5][C_2B_9H_{11}]Hf(CH_3)$ complex, on the other hand, is much more stable and requires heating in toluene for 40 hours at $75°$ C. in order to obtain the methylene-bridged derivative.

Generally conversion of the cyclopentadienyl dicarbollide complexes to the methylene-bridged derivatives can be effected by heating in an inert liquid solvent at a temperature of from $30°$ C. to $120°$ C., preferably from $40°$ C. to $80°$ C. Atmospheric pressure may be employed, or reduced pressure may be employed if desired to assist in methane degasification. The time required to effect complete conversion depends upon the temperature employed, with shorter times being required at the more elevated temperatures. Generally, complete conversion can be effected within 1 to 48 hours. An inert atmosphere should be maintained to prevent oxidation from occuring.

The novel cyclopentadienyl dicarbollide complexes of the present invention, and the methylene-bridged derivatives derived therefrom, can be employed to polymerize ethylene, in the absence of a cocatalyst, to produce polymers having a very low molecular weight and a narrow molecular weight distribution. Polymerization is effected by contacting ethylene, or a mixture of ethylene and at least one alpha olefin having 3 to 8 carbon atoms, with the complex or methylene-bridged derivative, in an inert liquid hydrocarbon By an "inert" liquid hydrocarbon is meant a liquid hydrocarbon which is non-reactive under the polymerization conditions employed. While the hydrocarbon selected need not function as solvent for the complex or methylene-bridged derivative, or the polymers obtained by the process, it usually serves as solvent for the monomers employed in the polymerization. Among the inert liquid hydrocarbons suitable for this purpose may be mentioned isopentane, hexane, cyclohexane, heptane, benzene, toluene and the like. Generally, the inert liquid hydrocarbon is employed with the complex or methylene-bridged derivative in such amount that the mixture contains from 0.001 weight percent to 75 weight percent of the complex or methylene-bridged derivative. If desired, less concentrated or more concentrated mixtures can be employed.

The alpha-olefins which may be polymerized with ethylene contain from 3 to 8 carbon atoms per molecule. These alpha-olefins should not contain any branching on any of their atoms closer than two carbon atoms removed from the double bond. Suitable alpha-olefins include propylene, butene-1, pentene-1, hexene-1, 4-methylpentene-1, heptene-1 and octene-1. The preferred alpha-olefins are propylene, butene-1, hexene-1, 4-methylpentene-1, and octene-1.

Contact between the ethylene monomer, or mixture of ethylene monomer and at least one alpha olefin monomer having from 3 to 8 carbon atoms, and the cyclopentadienyl dicarbollide complex, or methylene-bridged derivative derived therefrom, can be effected by continuously bubbling ethylene, or mixture of ethylene and higher alpha olefin monomer, through the inert liquid hydrocarbon containing such complex or methylene-bridged derivative. Alternatively, contact can be effected by sealing a fixed amount of ethylene, or mixture of ethylene and higher alpha olefin monomer, in a polmerization reactor containing such complex or methylene-bridged derivative, and allowing polymerization to proceed under autogeneous pressure with, if desired, further batchwise additions of ethylene or mixture of ethylene and higher alpha olefin monomer. In any event, reactive contact between the ethylene monomer, or mixture of ethylene and higher alpha olefin monomer, and the complex or methylene-bridged derivative, should be maintained by constant stirring or agitation of the reaction mixture.

The pressures employed in effecting polymerization can vary over a wide range. If desired, polymerization can be effected at atmospheric pressure; however, pressures both above and below atmospheric pressure, for example pressures ranging from as low as 5 psi to as high as 7500 psi, can also be employed whenever it is desirable to do so.

Polymerization readily occurs at temperatures ranging from as low as $-10°$ C. to as high as 200° C., but it is preferably effected at temperatures ranging from about 10° C. to about 90° C. Temperatures both above and below the broadly disclosed range can also be employed; however, no commensurate advantages are obtained by employing temperatures outside the limits of the broadly disclosed range.

If desired, polymerization may be conducted in the presence of an inert gas, i.e., a gas which is nonreactive under the conditions employed during polymerization. A chain transfer agent, such as hydrogen, may also be present. The reactor should, however, be maintained substantially free of undesirable catalyst poisons, such as moisture, oxygen, carbon monoxide, carbon dioxide, acetylene, and the like. For this reason, it is preferred that polymerization be conducted in the presence of an alkylaluminum compound which serves as scavenger for these poisons.

The alkylaluminum compounds which can be employed together with the cyclopentadienyl dicarbollide complexes or the methylene-bridged derivatives derived therefrom have the formula $$Al(R')_3$$

wherein R' is a saturated hydrocarbon radical containing from 1 to 14 carbon atoms, which radicals may be the same or different. Such radicals may be substituted with one or more substituents which are inert under the reaction conditions employed during polymerization. Preferably R' is an alkyl radical containing 2 to 8 carbon atoms.

It is not known for certain whether the alkylaluminum compound functions as a cocatalyst or merely as an impurity scavenger. In any event, such compound is employed in a molar ratio of from 1:1 to 1000:1 of the cyclopentadienyl dicarbollide complex or the methylene-bridged derivative.

The ethylene polymers produced are characterized by a very low molecular weight, a narrow molecular weight distribution, and high vinyl unsaturation. Generally, such polymers have a weight average molecular weight ($M_w$) of from about 250 to about 500,000, a number average molecular weight ($M_n$) of from about 100 to about 200,000, a molecular weight distribution ($M_2/M_n$) of from about 1.5 to about 5.0, and a vinyl unsaturation of about 5 to about 100 per 1000 carbon atoms.

The novel cyclopentadienyl dicarbollide complexes of the present invention, and the methylene-bridged derivatives derived therefrom, can also be employed to oligomerize propylene. Oligomerization is effected by contacting propylene with the complex or methylene-bridged derivative. If desired, an inert liquid hydrocarbon may be employed as a diluent. Reactive contact between the complex or methylene-bridged derivative and the propylene should be maintained by constant stirring or agitation.

The pressures employed in effecting oligomerization can vary over a wide range. If desired, oligomerization can be effected at atmospheric pressure; however, pressures both above and below atmospheric pressure, for example pressures ranging from as low as 5 psi to as high as 7500 psi, can also be employed whenever it is desirable to do so.

Oligomerization readily occurs at temperatures ranging from as low as $-10°$ C. to as high as 200° C., but is preferably effected at temperatures ranging from about 10° C. to about 150° C. Temperatures both above and below the broadly disclosed range can also be employed; however, no commensurate advantages are obtained by employing temperatures outside the limits of the broadly disclosed range.

If desired, oligomerization may be conducted in the presence for inert gas, i.e., a gas which is nonreactive under the conditions employed during oligomerization. The reactor should, however, be maintained substantially free of undesirable catalyst poisons, such as moisture, oxygen, carbon monoxide, carbon dioxide, acetylene, and the like. For this reason, it is preferred that oligomerization be conducted in the presence of an alkylaluminum compound which serves as a scavenger for these poisons. The same alkylaluminum compounds suitable for use during polymerization can be employed for this purpose.

The following Examples are designed to illustrate the process of the present invention and are not intended as a limitation upon the scope thereof.

The properties of the polymers produced in the Examples were determined by the following test methods:

Melt Index (MI)

ASTM D-1238, Condition E. Measured at 190° C. and reported as grams per 10 minutes.

Activity

Activity values are normalized values based upon the grams of polymer produced per mmol of hafnium or zirconium in the catalyst per hour per 100 psi of ethylene polymerization pressure.

Molecular Weight Distribution, $M_w/M_n$

Determined by Size Exclusion Chromatography.
Method A: Cross-linked polystyrene column pore size sequence: 1 column less than 1000 Å, 3 columns of mixed 500 to $5 \times 10^7$ Å; 1,2,4-trichlorobenzene solvent at 140° C. with refractive index detection.

EXAMPLE 1

Preparation of [C$_5$(CH$_3$)$_5$][C$_2$B$_9$H$_{11}$]Zr(CH$_3$)

A solution Of 3.50 g. (12.9 mmol) of [C$_5$(CH$_3$)$_5$]Zr(CH$_3$)$_3$ in 50 ml. of toluene was prepared and cooled to −78° C. under a nitrogen atmosphere. A solution of 1.75 g. (13.0 mmol) of C$_2$B$_9$H$_{13}$ in 40 ml. of toluene was added to the precooled solution by cannula, and the reaction mixture was warmed to ambient temperature. Gas evolution (CH$_4$) was observed and an orange-yellow solid precipitated from solution.

The reaction mixture was stirred for two hours at 23° C. The solid precipitate was collected by filtration, washed three times with 30 ml. of hexane, and dried under high vacuum for 12 hours. The product weighed 4.51 g, representing a 94.0% yield.

Analysis. Calculated for C$_{13}$H$_{29}$B$_9$Zr: C, 41.76; H,7.82; Zr, 24.40. Found: C,42.06; H,7.62; Zr, 24.74.

EXAMPLE 2

Preparation [C$_5$(CH$_3$)$_5$][C$_2$B$_9$H$_{11}$]Hf(CH$_3$)

A solution of 3.2 g. (8.93 mmol) of [C$_5$(CH$_3$)$_5$]Hf(CH$_3$)$_3$ in 40 ml. of toluene was prepared and cooled to −78° C. under a nitrogen atmosphere. A solution of 1.30 g. (9.68 mmol) of C$_2$B$_9$H$_{13}$ in 30 ml. of toluene was added to the precooled solution by cannula over a period of 15 minutes. The nitrogen was removed under vacuum and the reaction mixture was warmed to ambient temperature. Gas evolution (CH$_4$) was observed as the temperature approached 0° C. and the initially colorless reaction mixture turned bright yellow.

The reaction mixture was maintained at ambient temperature and degassed occasionally over a period of 48 hours. Half of the toluene was then removed under vacuum. Fifty milliliters (50 ml.) of hexane were then added by vacuum-transfer at −78° C., causing precipitation of a bright yellow solid. The solid precipitate was then collected by filtration, washed three times with 20 ml. of hexane, and dried under high vacuum for 15 hours. The crude product was recrystallized from a 1:1 mixture of toluene/hexene at −35° C. The crystallized product was recovered by filtration and dried in a glass frit. The product weighed 2.6 g, representing a 63.4% yield.

Analysis. Calculated for C$_{13}$H$_{29}$B$_9$Hf: C, 33.86; H, 6.34. Found: C, 33.97; H, 6.33.

EXAMPLE 3

Preparation {[C$_5$(CH$_3$)$_5$][C$_2$B$_9$H$_{11}$]Zr}$_2$-μ(CH$_2$)

(a) A slurry of 0.50 g (13.4 mmol) of [C$_5$(CH$_3$)$_5$][C$_2$B$_9$H$_{11}$]Zr(CH$_3$) in 25 ml. of toluene was heated at 50° C. for 15 hours in a glove box under a nitrogen atmosphere. Half of the toluene was then removed under vacuum. Fifty milliliters (50 ml) of hexane were then added by vacuum-transfer at −78° C., causing precipitation of a brick red solid. The solid precipitate was then collected by filtration and dried under vacuum for 12 hours. The product weighed 0.39 g, representing a 79.6% yield.

Analysis. Calculated for C$_{25}$H$_{54}$B$_{18}$Zr$_2$: C, 41.04; H, 7.44. Found: C, 40.79; H, 7.69.

(b) A solution of 25 mg (0.0067 mmol) of [C$_5$(CH$_3$)$_5$][C$_2$B$_9$H$_{11}$]Zr(CH$_3$) in 0.4 ml. of toluene-d$_8$ was prepared and maintained at 50° C. in a glove box under a nitrogen atmosphere. The solution was monitored by $^1$H NMR to detect changes in composition. It was found that [C$_5$(CH$_3$)$_5$][C$_2$B$_9$H$_{11}$]Zr(CH$_3$) was converted to {[C$_5$(CH$_3$)$_5$][C$_2$B$_9$H$_{11}$]Zr}$_2$-(μ-CH$_2$) quantitatively over a period of 2 hours.

EXAMPLE 4

Preparation Of {[C$_5$(CH$_3$)$_5$][C$_2$B$_9$H$_{11}$]Hf}$_2$-(μ-CH$_2$)

A solution of [C$_5$(CH$_3$)$_5$][C$_2$B$_9$H$_{11}$]Hf(CH$_3$) in toluene-d$_8$ (0.032 M) was prepared and heated at 80° C. for 40 hours in a flame-sealed NMR tube. Conversion of [C$_5$(CH$_3$)$_5$][C$_2$B$_9$H$_{11}$]Hf(CH$_3$) to {[C$_5$(CH$_3$)$_5$][C$_2$B$_9$H$_{11}$]Hf}$_2$-(μ-CH$_2$) occurred in an 80% yield as determined by $^1$H NMR. The methylene-bridged complex was spectroscopic ally characterized but could not be isolated free of several unidentified minor products.

EXAMPLE 5

Polymerization Of Ethylene With [C$_5$(CH$_3$)$_5$][C$_2$B$_9$H$_{11}$]Zr(CH$_3$)

(a) A slurry of 10 mg of [C$_5$(CH$_3$)$_5$][C$_2$B$_9$H$_{11}$]Zr(CH$_3$) in 0.5 ml. of toluene-d$_8$ was prepared and sealed in a NMR tube under 2 atmospheres of ethylene. Polymerization occurred rapidly at room temperature as evidenced by the precipitation of white polyethylene within 1–5 minutes. Unreacted ethylene was not detected by $^1$H NMR. The polyethylene was characterized by comparison of spectra with known polyethylene.

(b) A 25 weight percent solution of triisobutylaluminum in hexane was prepared, and a 1.0 ml. aliquot of this solution was added to 100 additional ml. of hexane. The triisobutylaluminum was employed as a poison scavenger.

Approximately 15 mg of [C$_5$(CH$_3$)$_5$][C$_2$B$_9$H$_{11}$]Zr(CH$_3$) prepared as in Example 1 was dissolved in 20 ml. of toluene. This solution was then added to the solution of triisobutylaluminum in hexane. A nitrogen atmosphere was maintained at all time. The final solution contained 40 μmol of Zr.

A one-liter autoclave reactor was dried by heating at a temperature greater than 96° C. under a stream of nitrogen for 20 minutes. After cooling the reactor to 22° C., 500 ml. of hexane was added to the reactor, followed by the mixture containing the zirconium complex and the triisobutylaluminum scavenger. The reactor contents were stirred under a gentle flow of nitrogen, and the reactor was sealed. The temperature of the reactor was maintained at 22° C. and the reactor was pressurized to a pressure of 150 Psi with ethylene. Polymerization was allowed to continue for 30 minutes at this temperature during which time ethylene was continually added to the reactor to maintain the pressure constant. At the end of this time, the reactor was vented and opened.

The polymer recovered had an M$_w$ of 182,000, an M$_n$ of 58,200, and an M$_w$/M$_n$ of 3.12.

Catalyst activity was 450 g polymer/mmol Zr-hr-100 psi ethylene

EXAMPLE 6

Polymerization Of Ethylene With [C$_5$(CH$_3$)$_5$][C$_2$B$_9$H$_{11}$]Hf(CH$_3$)

(a) A solution of [C$_5$(CH$_3$)$_5$][C$_2$B$_9$H$_{11}$]Hf(CH$_3$) in toluene-d$_8$ (0.03 M) was prepared and sealed in a NMR tube under 2 atmospheres of ethylene. Polymerization occurred rapidly at room temperature as evidenced by the precipitation of white polyethylene within 1–5 minutes. Unreacted ethylene was not detected by $^1$H NMR.

The polyethylene was characterized by comparison of spectra with known polyethylene.

(b) A 25 weight percent solution of triisobutylaluminum in hexane was prepared, and a 0.6 ml. aliquot of this solution was added to 10% additional ml. of hexane. The triisobutylaluminum was employed as a poison scavenger.

Approximately 104 mg of $[C_5(CH_3)_5][C_2B_9H_{11}]Hf(CH_3)$ prepared as in Example 2 was dissolved in 20 ml. of toluene. A 2.5 ml. aliquot of this solution was then added to the solution of triisobutylaluminum in hexane. A nitrogen atmosphere was maintained at all times. The final solution contained 28 μmol of Hf.

A one-liter autoclave reactor was dried by heating at a temperature greater than 96° C. under a stream of nitrogen for 20 minutes. After cooling the reactor to 65° C., 500 ml. of hexane was added to the reactor, followed by the mixture containing the hafnium complex and the triisobutylaluminum scavenger. The reactor contents were stirred under a gentle flow of nitrogen, and the reactor was sealed. The reactor was then pressurized to a pressure of 150 psi with ethylene and heated until the desired polymerization temperature of 85° C. was attained. Polymerization was allowed to continue for 30 minutes at this temperature, during which time ethylene was continually added to the reactor to maintain the pressure constant. At the end of an hour, the reactor was vented and opened.

The polymer recovered had an $M_w$ of 653, an $M_n$ of 332, an $M_w/M_n$ of 1.97, and a vinyl unsaturation of 36 per 1000 carbon atoms.

Catalyst activity was 5400 g polymer/mmol Hf-hr-100 psi ethylene.

(c) Ethylene was polymerized as in (b) above except that the reactor was pressurized to a pressure of 10 psi with hydrogen before being pressurized to a pressure of 150 psi with ethylene.

The polymer recovered had an $M_w$ of 647, an $M_n$ of 322, an $M_w/M_n$ of 2.01, and a vinyl unsaturation of 35 per 1000 carbon atoms.

Catalyst activity was 5800 g polymer/mmol Hf-hr-100 psi ethylene.

(d) Ethylene was polymerized as in (b) above except that a 1.3 ml aliquot of the 25 weight percent solution of triisobutylaluminum in hexane and a 6 ml. aliquot of a toluene solution containing 50 μmol of Hf were employed, and polymerization was conducted at a temperature of 25° C. rather than 85° C.

Catalyst activity was 130 g polymer/mmol Hf-hr-100 psi ethylene.

EXAMPLE 7

Oligomerization Of Propylene With $[C_5(CH_3)_5][C_2B_9H_{11}]Zr(CH_3)$

A slurry of 10 mg of $[C_5(CH_3)_5][C_2B_9H_{11}]Zr(CH_3)$ in 0.5 ml. of toluene-$d_8$ was prepared and sealed in a NMR tube under 2 atmospheres of propylene. After complete conversion of propylene, as determined by NMR, the NMR tube was cracked open and the volatiles collected by trap to trap distillation. The volatiles were examined by $^1H$ NMR and found to be mostly 2-methylpentene and 2,4-dimethylheptene. Isobutene was identified by GC.

EXAMPLE 8

Oligomerization Of Propylene With $[C_5(CH_3)_5][C_2B_9H_{11}]Hf(CH_3)$ (a) A solution of $[C_5(CH_3)_5][C_2B_9H_{11}]Hf(CH_3)$ in toluene-$d_8$ (0.03 M) was prepared and sealed in a NMR tube under 2 atmospheres of propylene. After complete conversion of propylene, as determined by NMR, the NMR tube was cracked open and the volatiles collected by trap to trap distillation. The volatiles were examined by $^1H$ NMR and found to be mostly 2-methylpentene and 2,4-dimethylheptene. Isobutene was identified by GC.

(b) A 25 weight percent solution of triisobutylaluminum in hexane was prepared, and a 1.2 ml. aliquot of this solution was added to 20 additional ml. of hexane. The triisobutylaluminum was employed as a poison scavenger.

Approximately 100 mg of $[C_5(CH_3)_5][C_2B_9H_{11}]Hf(CH_3)$ prepared as in Example 2 was dissolved in 20 ml. of toluene. A 5.0 ml. aliquot of this solution was then added to the solution of triisobutylaluminum in hexane. A nitrogen atmosphere was maintained at all times. The final solution contained 56 μmol of Hf.

A one-liter autoclave reactor was dried by heating at a temperature greater than 96° C. under a stream of nitrogen for 20 minutes. After cooling the reactor to 15° C., the mixture containing the hafnium complex and the triisobutylaluminum scavenger was transferred to the reactor, followed by 800 ml. of liquid propylene. The reactor was then sealed and the temperature raised to 40° C. over a period of 5 minutes. Polymerization was allowed to continue for 60 minutes at this temperature. At the end of this time, the reactor was vented and opened. GC/MS analysis of the homogeneous reactor solution detected 4 turnovers of $C_9$ to $C_{15}$ oligomers. This represented a yield of 0.03 g and an activity of 0.5 g of oligomer/mmol Hf.

EXAMPLE 9

Oligomerization Of Propylene With $\{[C_4(CH_3)_5][C_2B_9H_{11}]Zr\}_2$-$(\mu$-$CH_2)$ A 25 weight percent solution of triisobutylaluminum in hexane was prepared, and a 1.0 ml. aliquot of this solution was added to 20 additional ml. of hexane. The triisobutylaluminum was employed as a poison scavenger.

Approximately 195 mg of $\{[C_5(CH_3)_5][C_2B_9H_{11}]Zr\}_2$-$(\mu$-$CH_2)$ was dissolved in 20 ml. of toluene. A 2.0 ml. aliquot of this solution was then added to the solution of triisobutylaluminum in hexane. A nitrogen atmosphere was maintained at all times. The final solution contained 50 μmol of Zr.

A one-liter autoclave reactor was dried by heating at a temperature greater than 96° C. under a stream of nitrogen for 20 minutes. After cooling the reactor to 15° C., the mixture containing the zirconium complex and the triisobutylaluminum scavenger was transferred to the reactor, followed by 800 ml. of liquid propylene. The reactor was sealed and the temperature raised to 40° C. over a period of 10 minutes. Polymerization was allowed to continue for 60 minutes at this temperature. At the end of this time, the reactor was vented and opened. GC/MS analysis of the homogeneous reactor solution detected approximately 180 turnovers of $C_9$ to $C_{15}$ oligomers. This represented a 1.6 g yield and an activity of 30 g of oligomer/mmol Zr.

EXAMPLE 10

Polymerization Of Ethylene With $\{[C_5(CH_3)_5][C_2B_9H_{11}]Zr\}_2\text{-}(\mu\text{-}CH_2)$ (a) A 25 weight percent solution of triisobutylaluminum in hexane was prepared, and a 1.0 ml. aliquot of this solution was added to 100 additional ml. of hexane. The triisobutylaluminum was employed as a poison scavenger.

Approximately 195 mg of $\{[C_5(CH_3)_5][C_2B_9H_{11}]Zr\}_2\text{-}(\mu\text{-}CH_2)$ was dissolved in 20 ml. of toluene. A 1.0 ml. aliquot of this solution was then added to the solution of triisobutylaluminum in hexane. A nitrogen atmosphere was maintained at all times. The final solution contained 25 μmol of Zr.

A one-liter autoclave reactor was dried by heating at a temperature greater than 96° C. under a stream of nitrogen for 20 minutes. After cooling the reactor to 65° C., 500 ml. of hexane was added to the reactor, followed by the mixture containing the zirconium complex and the triisobutylaluminum scavenger. The reactor contents were stirred under a gentle flow of nitrogen, and the reactor was sealed. The reactor was then pressurized to a pressure of 150 psi with ethylene and heated until the desired polymerization temperature of 85° C. was attained. Polymerization was allowed to continue at this temperature for 30 minutes, during which time ethylene was continually added to the reactor to maintain the pressure constant. At the end of this time, the reactor was vented and opened.

The polymer recovered had an $M_w$ of 3620, an $M_n$ of 1930, an $M_w/M_n$ of 1.88, and a vinyl unsaturation of 7.5 per 1000 carbon atoms.

Catalyst activity was 3970 g polymer/mmol Zr-hr-100 psi ethylene.

(b) Ethylene was polymerized as in (a) above except that the reactor was pressurized to a pressure of 1 psi with hydrogen before being pressurized to a pressure of 150 psi with ethylene.

The polymer had an Mw of 2550, an $M_n$ of 942, an $M_w/M_n$ of 2.70, and a vinyl unsaturation of 7.8 per 1000 carbon atoms.

Catalyst activity was 4400 g polymer/mmol Zr-hr-100 psi ethylene.

(c) Ethylene was polymerized as in (a) above except that polymerization was conducted at a temperature of 15° C. rather than 85° C.

Catalyst activity was 110 g polymer/mmol Zr-hr-100 psi ethylene.

COMPARATIVE EXAMPLE 10

Ethylene was polymerized as in Example 10(a) except that methylalumoxane (MAO) was employed as a potential cocatalyst. The reaction mixture contained an Al/Zr ratio of 750.

The polymer had a melt index of 92 dg/min.

Catalyst activity was 1880 g polymer/mmol Zr-hr-100 psi ethylene, showing that activity is not increased in the presence of MAO. This suggests that MAO is not an effective cocatalyst.

We claim:

1. Cyclopentadienyl dicarbollide complex of the formula:

$$(Cp')(C_2B_9H_{11})M(CH_3)$$

wherein:
Cp' is an unsubstituted, alkyl-substituted, or fused ring cyclopentadienyl radical, and
M is Ti, Zr or Hf.

2. Cyclopentadienyl dicarbollide complex as in claim 1 wherein M is Zr.

3. Cyclopentadienyl dicarbollide complex as in claim 1 wherein M is Hf.

4. Cyclopentadienyl dicarbollide complex as in claim 1 wherein Cp' is $C_5H_5$ or $C_5(CH_3)_5$.

5. Cyclopentadienyl dicarbollide complex as in claim 4 wherein M is Zr.

6. Cyclopentadienyl dicarbollide complex as in claim 4 wherein M is Hf.

7. A process for producing a cyclopentadienyl dicarbollide complex of the formula $$(Cp')(C_2B_9H_{11})M(CH_3)$$

wherein:
Cp' is an unsubstituted, alkyl-substituted, or fused ring cyclopentadienyl radical, and
M is Ti, Zr or Hf,
which comprises reacting nido-$C_2B_9H_{13}$ and a cyclopentadienyl metallocene complex of the formula:

$$(Cp')M(CH_3)_3$$

wherein Cp' and M are as above defined.

8. A process as in claim 7 wherein M is Zr.
9. A process as in claim 7 wherein M is Hf.
10. A process as in claim 7 wherein Cp' is $C_5H_4$ or $C_5(CH_3)_5$.
11. A process as in claim 10 wherein M is Zr.
12. A process as in claim 10 wherein M is Hf.

* * * * *